Figure 1:
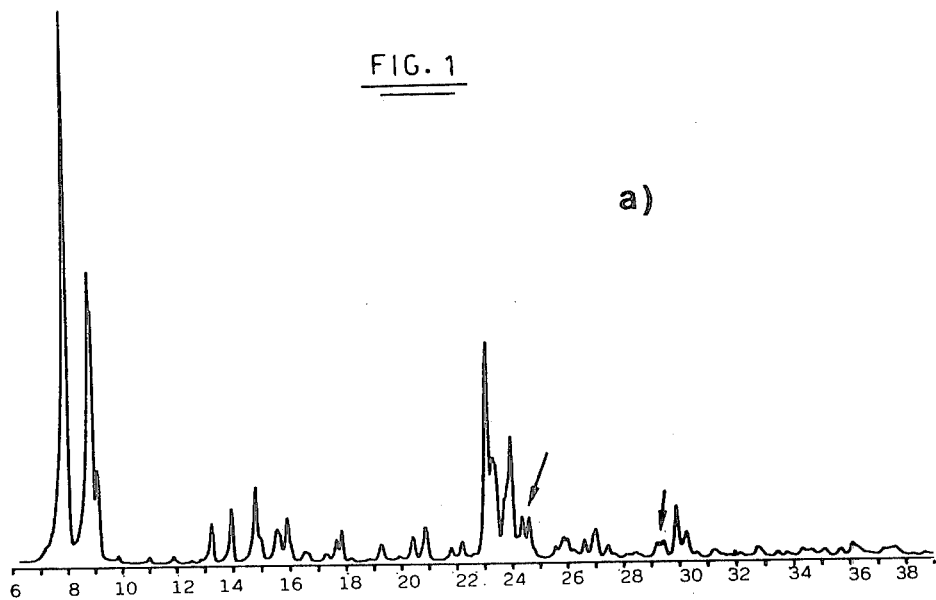
Figure 1:
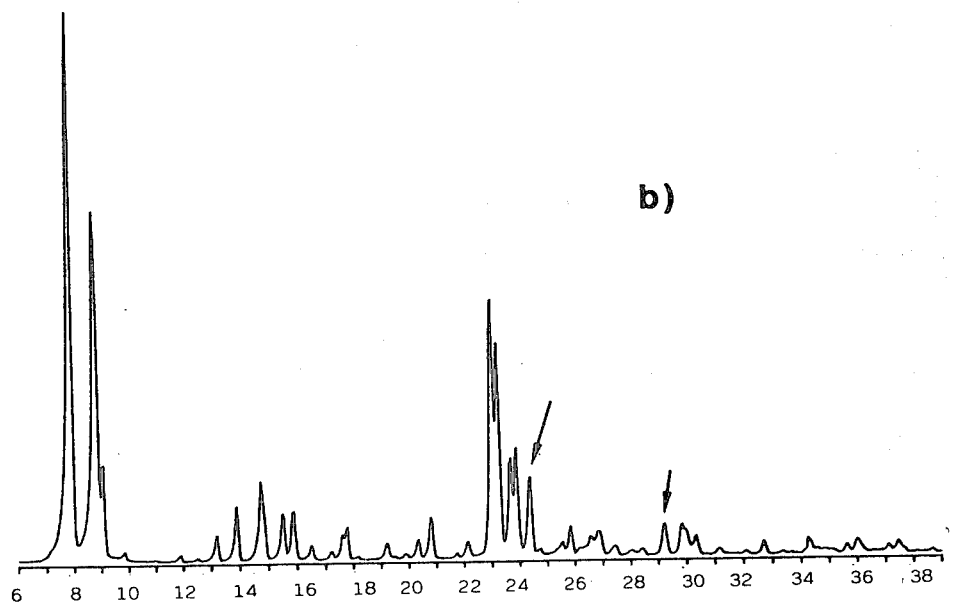

United States Patent [19]
Neri et al.

[11] Patent Number: 4,476,327
[45] Date of Patent: Oct. 9, 1984

[54] PROCESS FOR THE SYNTHESIS OF GLYCOL MONOMETHYLETHERS

[75] Inventors: Carlo Neri; Franco Buonomo, both of S. Donato Milanese; Bartolomeo Anfossi, Milan, all of Italy

[73] Assignee: Anic S.p.A., Palermo, Italy

[21] Appl. No.: 513,798

[22] Filed: Jul. 14, 1983

[30] Foreign Application Priority Data

Jul. 28, 1982 [IT] Italy .............................. 22605 A/82

[51] Int. Cl.$^3$ ............................................. C07C 41/05
[52] U.S. Cl. .................................... 568/678; 568/678;
   568/159; 568/626; 568/697; 568/662; 568/660
[58] Field of Search ............... 568/678, 670, 659, 626, 568/697, 662, 660

[56] References Cited

U.S. PATENT DOCUMENTS 2,808,442 10/1957 Smith .................................. 568/697

Primary Examiner—Howard T. Mars
Attorney, Agent, or Firm—Hedman, Gibson, Costigan & Hoare

[57] ABSTRACT

A process for the synthesis of glycol monomethylethers consisting of reacting an olefin compound, methanol and hydrogen peroxide in aqueous solution in the presence of synthetic zeolites containing titanium atoms, of general formula:

$$x\text{TiO}_2 \cdot (1-x)\text{SiO}_2,$$

where x lies between 0.0001 and 0.04.

5 Claims, 2 Drawing Figures a)

b)

PROCESS FOR THE SYNTHESIS OF GLYCOL MONOMETHYLETHERS

This invention relates to a process for the synthesis of glycol monomethylethers in which the synthesis reaction is carried out in a single stage.

It is known to prepare glycol monomethylethers by reacting an epoxide with methanol, using an acid as catalyst.

These preparation methods have the drawback of requiring several reaction stages.

We have now surprisingly found that a synthetic zeolite containing titanium atoms is able to cause an olefin, methanol and hydrogen peroxide to react together in aqueous solution in a single stage, to give monomethylethers.

The subject matter of the present invention is a process for the synthesis of glycol monomethylethers consisting of reacting an olefinic compound, methanol and hydrogen peroxide in aqueous solution in the presence of synthetic zeolites containing titanium atoms (titanium silicalites), of the following general formula:

$$xTiO_2.(1-x)SiO_2,$$

where x lies between 0.0001 and 0.04.

The synthetic zeolites used for the epoxidation reaction are described in Belgian Pat. No. 886,812, of which we repeat some points illustrating the material and relative method of preparation. The composition range of the titanium silicalite expressed in terms of molar ratios of the reagents is as follows:

| Molar ratio of reagents | | preferably |
|---|---|---|
| $SiO_2/TiO_2$ | 5-200 | 35-65 |
| $OH^-/SiO_2$ | 0.1-1.0 | 0.3-0.6 |
| $H_2O/SiO_2$ | 20-200 | 60-100 |
| $Me/SiO_2$ | 0.0-0.5 | 0 |
| $RN/SiO_2$ | 0.1-2.0 | 0.4-1.0 |

$RN^+$ indicates the nitrogenated organic cation deriving from the organic base used for the preparation of the titanium silicalite (TS-1).

Me is an alkaline ion, preferably Na or K.

The final TS-1 has a composition satisfying the formula $xTiO_2.(1-x)SiO_2$, where x lies between 0.0001 and 0.04, and preferably between 0.01 and 0.025. The TS-1 is of the silicalite type, and all the titanium substitutes the silicon.

The synthetic material has characteristics which are shown up by X-ray and infrared examination.

The X-ray examination is carried out by means of a powder diffractometer provided with an electronic pulse counting system, using the radiation $CuK\lambda^-$. The titanium silicalites (TS-1) are characterised by a X-ray diffraction spectrum as shown in FIG. 1b. This spectrum is similar overall to the typical spectrum of silicalite (FIG. 1a), however it has certain clearly "single" reflections where double reflections are evident in the pure silicalite spectrum.

Because the spectral differences between TS-1 and silicalite are relatively small, special accuracy is required in the spectral determination. For this reason TS-1 and silicalite were examined by the same apparatus, using $Al_2O_3$ as the internal standard. Table 1 shows the most significant spectral data of a TS-1 where x=0.017, and of a pure silicalite.

The constants of the elementary crystalline cell were determined by the minimum square method, on the basis of the interplanar distances of 7-8 single reflections lying within the range of 10°-40° 2θ.

A large proportion of the interplanar distances of TS-1 are tendentially greater than the corresponding distances of pure silicalite, although only slightly, which is in accordance with the larger predictable value of the Ti—O bond distance relative to that of the Si—O bond distance.

Passage from a double reflection to a single reflection is interpreted as a change from a monoclinic symmetry (pseudo orthorhombic) (silicalite) to an effective orthorhombic symmetry, "titanium silicalite" (TS-1). In FIG. 1, the most apparent aforesaid spectral differences are indicated by arrows.

INFRARED EXAMINATION

TS-1 shows a characteristic absorption band at about 950 cm$^{-1}$ (see FIG. 2, spectra B, C and D) which is not present in the pure silicalite spectrum (FIG. 2, spectrum A), and is also absent in titanium oxides (rutile, anastase) and in alkaline titanates.

Spectrum B is that of TS-1 with 5 mol% of $TiO_2$, spectrum C is that of TS-1 with 8 mol% of $TiO_2$, and spectrum D is that of TS-1 with 2.3 mol% of $TiO_2$.

Figure 2:
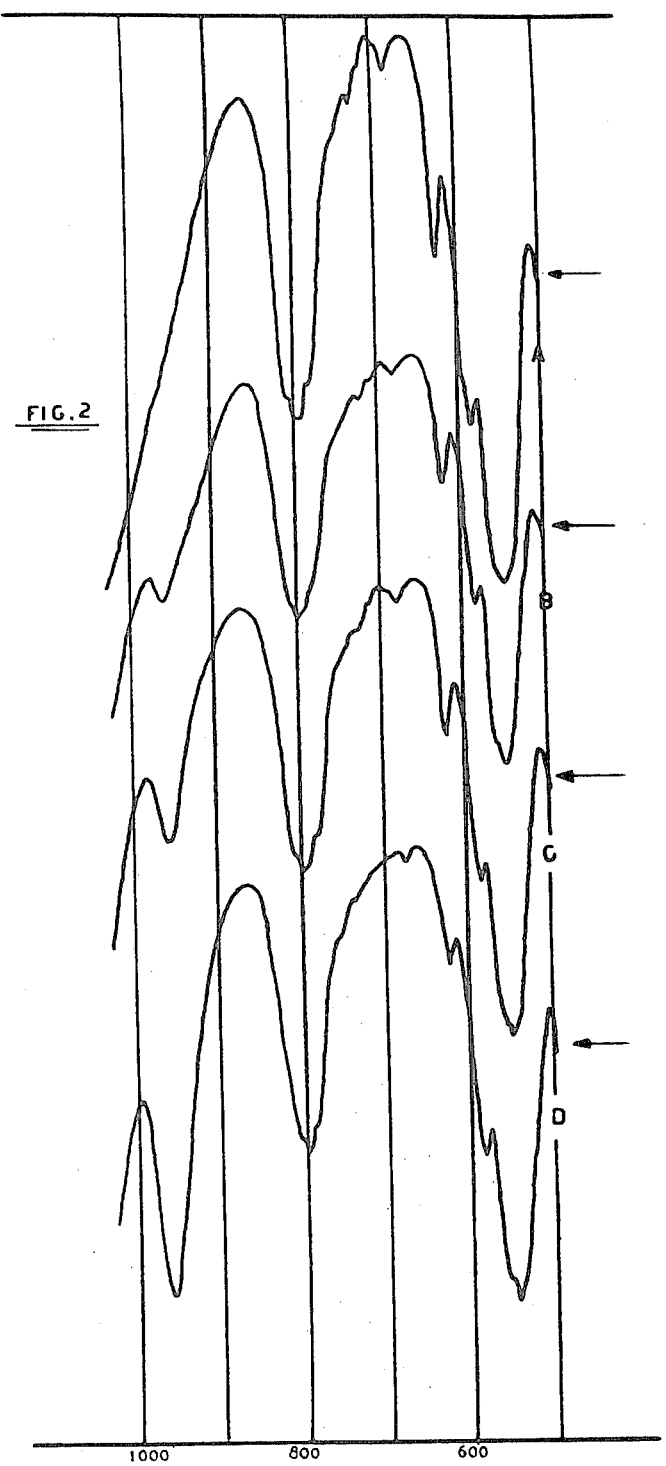

As can be seen from FIG. 2, the band intensity at approximately 950 cm$^{-1}$ increases with the quantity of titanium which substitutes the silicon in the silicalite structure.

MORPHOLOGY

From a morphological aspect, TS-1 is in the form of parallelepipeds with chamfered edges. A X-ray microprobe examination has shown that the titanium distribution within the crystal is perfectly uniform, thus confirming that the titanium substitutes the silicon in the silicalite structure, and is not present in other forms.

The process for preparing titanium silicalite comprises the preparation of a reaction mixture consisting of sources of silicon oxide, titanium oxide and possibly an alkaline oxide, a nitrogenated organic base and water, the composition in terms of the molar reagent ratios being as heretofore defined.

The silicon oxide source can be a tetraalkylorthosilicate, preferably tetraethylorthosilicate, or simply a silicate in colloidal form, or again a silicate of an alkaline metal, preferably Na or K.

The titanium oxide source is a hydrolysable titanium compound preferably chosen from $TiCl_4$, $TiOCl_2$ and $Ti(alkoxy)_4$, preferably $Ti(OC_2H_5)_4$.

The organic base is tetraalkylammonium hydroxide, and in particular tetrapropylammonium hydroxide.

The reagent mixture is subjected to hydrothermal treatment in an autoclave at a temperature of between 130° and 200° C. under its own developed pressure, for a time of 6-30 days until the crystals of the TS-1 precursor are formed. These are separated from the mother solution, carefully washed with water and dried. When in the anhydrous state they have the following composition:

$$xTiO_2.(1-x)SiO_2.0.04(RN^+)_2O.$$

The precursor crystals are heated for between 1 and 72 hours in air at 550° C. to completely eliminate the nitrogenated organic base. The final TS-1 has the following composition:

$$xTiO_2 \cdot (1-x)SiO_2,$$

where x is as heretofore defined.

Chemical and physical examinations are carried out on the products thus obtained.

The glycol monomethylether synthesis reaction is as follows:

$$R-CH=CH-R' + H_2O_2 + CH_3OH \longrightarrow$$

$$R-\underset{OH}{\underset{|}{C}H}-\underset{OCH_3}{\underset{|}{C}H}-R' + H_2O$$

where R and R', which can be the same or different, can be H, or an alkyl, aryl, alkylaryl, cycloalkyl or alkylcycloalkyl radical. The methanol can be replaced by another alcohol.

The products obtained can be used as solvents, as intermediates or as "solutizers" for methanol in petrols.

The optimum reaction temperature is between 50° and 150° C., and preferably about 100° C. At lower temperatures more epoxide and less ether are obtained. The pressure is that suitable for maintaining the olefin compound dissolved in the methanol.

The reactions can also be carried out with $H_2O_2$ in aqueous solution at low concentration (10-70% w/v).

By way of example, the olefins which can be used for the synthesis of glycol monomethylethers by this process are ethylene, propylene, butene-1, cis butene-2, trans butene-2 and isobutene.

Some examples are given hereinafter in order to better illustrate the invention, but these are not to be taken as limitative thereof in any way.

EXAMPLES 1-6

100 cc of methanol, 3 g of catalyst and 50 g of olefin are fed into a 250 cc stainless steel autoclave fitted with a magnetic stirrer, an inlet for feeding the reagents and a dip tube for solution withdrawal.

The autoclave is immersed in a bath temperature-controlled at 100° C., and, using a metering pump, a quantity of 36% w/v $H_2O_2$ is fed equal to 60 mol% of the olefin. The progress of the reaction with time is followed by withdrawing samples of the $H_2O_2$ and titrating. When $H_2O_2$ is no longer present, the reaction is interrupted and the products are analyzed by chromatograph.

The results are given in Table 2.

The same reactions can be carried out with the catalyst on a fixed bed by pumping the olefin/methanol solution and the $H_2O_2$ solution using two metering pumps which are preset such that the molar $H_2O_2$/olefin ratio is about 0.6.

EXAMPLES 7-10

In order to demonstrate that dilution of the $H_2O_2$ with water is not essential for the purposes of the reaction according to the invention, tests were carried out under the conditions of Examples 1-6, using butene-2 and propylene with 10% w/v and 70% w/v $H_2O_2$, and maintaining the feed ratio unaltered at 60%.

The results are shown in Table 3.

TABLE 1

| TS-1 | | | Silicalite[a] | | |
|---|---|---|---|---|---|
| $2\sigma$ (Cuk$\alpha$) | Interplanar distance d(Å) | Rel. Int.[b] | $2\sigma$ (Cuk$\alpha$) | Interplanar distance d(Å) | Rel. Int.[b] |
| 7.94 | 11.14 | vs | 7.94 | 11.14 | vs |
| 8.85 | 9.99 | s | 8.85 | 9.99 | s |
| 9.08 | 9.74 | m | 9.08 | 9.74 | m |
| 13.21 | 6.702 | w | 13.24 | 6.687 | w |
| 13.92 | 6.362 | mw | 13.95 | 6.348 | mw |
| 14.78 | 5.993 | mw | 14.78 | 5.993 | mw |
| 15.55 | 5.698 | w | 15.55 | 5.698 | w* |
| 15.90 | 5.574 | w | 15.90 | 5.574 | w |
| 17.65 | 5.025 | w | 17.65 | 5.025 | w |
| 17.81 | 4.980 | w | 17.83 | 4.975 | w |
| 20.37 | 4.360 | w | 20.39 | 4.355 | w |
| 20.85 | 4.260 | mw | 20.87 | 4.256 | mw |
| 23.07 | 3.855 | s | 23.08 | 3.853 | s |
|  |  |  | 23.28 | 3.821 | ms |
| 23.29 | 3.819 | s |  |  |  |
|  |  |  | 23.37 | 3.806 | ms |
|  |  |  | 23.71 | 3.753 | ms |
| 23.72 | 3.751 | s |  |  |  |
|  |  |  | 23.80 | 3.739 | ms |
| 23.92 | 3.720 | s | 23.94 | 3.717 | s |
|  |  |  | 24.35 | 3.655 | mw |
| 24.41 | 3.646 | m |  |  |  |
|  |  |  | 24.60 | 3.619 | mw |
|  |  |  | 25.84 | 3.448 | w |
| 26.87 | 3.444 | w |  |  |  |
|  |  |  | 25.97 | 3.431 | w |
| 26.87 | 3.318 | w* | 26.95 | 3.308 | w* |
|  |  |  | 29.23 | 3.055 | w |
| 29.27 | 3.051 | mw |  |  |  |
|  |  |  | 29.45 | 3.033 | w |
| 29.90 | 2.988 | mw | 29.90 | 2.988 | mw |
| 30.34 | 2.946 | w | 30.25 | 2.954 | w |
| 45.00 | 2.014 | mw* | 45.05 | 2.012 | mw* |
| 45.49 | 1.994 | mw* | 45.60 | 1.989 | mw* |

[a]Prepared by the method of U.S. Pat. No. 4,061,724; product calcined at 550° C.
[b]vs: very strong; s: strong; ms: medium-strong; m: medium; mw: medium-weak; w: weak; *: multiplet.

TABLE 2

| Ex. No. | OLEFIN | TIME hours | $H_2O_2$ CONVERSION % | ETHER YIELD | OTHERS |
|---|---|---|---|---|---|
| 1 | ethylene | 0.5 | 100 | 98.5 | The remainder to 100% |
| 2 | propylene | 0.5 | " | 99.3 | consists of small quantities |
| 3 | butene-1 | 1 | " | 94.6 | of epoxide which can be |
| 4 | cis butene-2 | 1 | " | 96.8 | recycled to the reaction |
| 5 | trans butene-2 | 1 | " | 95.4 |  |
| 6 | isobutene | 0.8 | " | 99.2 | The ether yield is represented by: $\frac{\text{moles of ether formed}}{\text{moles of } H_2O_2 \text{ reacted}} \times 100$ |

TABLE 3

| Ex. No. | OLEFIN | $H_2O_2$ % w/v | TIME hours | $H_2O_2$ CONVERSION % | ETHER YIELD % | OTHERS |
|---|---|---|---|---|---|---|
| 7 | butene-2 | 10 | 1 | 100 | 93.8 | The remainder to 100% |
| 8 | butene-2 | 70 | 1 | 100 | 95.6 | consists of small quantities |
| 9 | propylene | 10 | 0.5 | 100 | 98.6 | of epoxide which can be |
| 10 | propylene | 70 | 0.5 | 100 | 98.5 | recycled to the reaction |

We claim:

1. A process for the synthesis of glycol monomethyl ethers, characterised by reacting together an olefin compound, methanol and hydrogen peroxide in aqueous solution, in the presence of synthetic zeolites containing titanium atoms, of general formula:

$$xTiO_2 \cdot (1-x)SiO_2$$

where x lies between 0.0001 and 0.04.

2. A process as claimed in claim 1, characterised in that the reaction is carried out at a temperature of between 50° and 150° C.

3. A process as claimed in claim 1, wherein the hydrogen peroxide is in dilute aqueous solution.

4. A process as claimed in claim 1, wherein the hydrogen peroxide in the aqueous solution is between 10 and 70% w/v.

5. A process as claimed in claim 1, wherein the olefin compound is chosen from ethylene, propylene, butene-1, cis butene-2, trans butene-2 and isobutene.

* * * * *